US00PP16790P2

(12) United States Plant Patent
Sakazaki

(10) Patent No.: US PP16,790 P2
(45) Date of Patent: Jul. 11, 2006

(54) ***SATUROZYGIS* PLANT NAMED 'USMINT2'**

(50) Latin Name: ***Saturozygis (Satureja×Hesperozygis)* hybrid**
Varietal Denomination: Usmint2

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 38 days.

(21) Appl. No.: 11/045,975

(22) Filed: Jan. 28, 2005

(51) Int. Cl.
*A01H 5/00* (2006.01)

(52) U.S. Cl. ..... Plt./226
(58) Field of Classification Search ..... Plt./226
See application file for complete search history.

(56) References Cited

PUBLICATIONS www.inspection.gc.ca/english/plaveg/pbrpov/cropreport/sate.shtml.*
copf.org/auwa/pdf/PBR%20apps%20accepted%20–%20Nov%202004.pdf*

* cited by examiner

* cited by examiner

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Saturozygis* plant named 'Usmint2', characterized by its upright and outwardly spreading plant habit; freely branching growth habit; mint-scented leaves; and light red purple-colored flowers.

1 Drawing Sheet

Botanical designation: *Saturozygis* (*Satureja×Hesperozygis*) hybrid.
Cultivar denomination: 'Usmint2'.

BACKGROUND OF THE INVENTION

The present Invention relates to a new and distinct cultivar of *Saturozygis* plant, botanically known as *Saturozygis* (*Satureja×Hesperozygis*) hybrid, and hereinafter referred to by the name 'Usmint2'.

The new *Saturozygis* is a product of a planned breeding program conducted by the Inventor in Hikone Shiga, Japan. The new *Saturozygis* originated from an interspecific cross-pollination made by the Inventor on May 25, 1999, of an unnamed selection of *Satureja mexicana*, not patented, as the female, or seed, parent with an unnamed selection of *Hesperozygis* sp., not patented, as the male, or pollen, parent. The new *Saturozygis* was discovered and selected by the Inventor as a single flowering plant within the progeny of the stated cross-pollination grown in a controlled environment in Bonsall, Calif. on May 12, 2000.

Asexual reproduction of the new cultivar by terminal cuttings taken at Bonsall, Calif., since Jul. 1, 2000, has shown that the unique features of this new *Saturozygis* are stable and reproduced true to type in successive generations.

SUMMARY OF THE INVENTION

Plants of the cultivar Usmint2 have not been observed under all possible environmental conditions. The phenotype may vary somewhat with variations in environment such as temperature and light intensity without, however, any variance in genotype.

The following traits have been repeatedly observed and are determined to be the unique characteristics of 'Usmint2'. These characteristics in combination distinguish 'Usmint2' as a new and distinct cultivar:

1. Upright and outwardly spreading plant habit.
2. Freely branching growth habit.
3. Mint-scented leaves.
4. Light red purple-colored flowers.

Plants of the new *Saturozygis* can be compared to plants of the female parent, the unnamed selection of *Satureja mexicana*. Plants of the new *Saturozygis* differ from plants of the female parent selection in the following characteristics:

1. Plants of the new *Saturozygis* are more vigorous than plants of the female parent selection.
2. Plants of the new *Saturozygis* flower for a longer period of time than plants of the female parent selection.
3. Plants of the new *Saturozygis* and the female parent selection differ in flower coloration as plants of the female parent selection have orange-colored flowers.

Plants of the new *Saturozygis* can be compared to plants of the male parent, the unnamed selection of *Hesperozygis* sp. Plants of the new *Saturozygis* differ from plants of the male parent selection in the following characteristics:

1. Plants of the new *Saturozygis* are more vigorous than plants of the male parent selection.
2. Plants of the new *Saturozygis* flower for a longer period of time than plants of the male parent selection.
3. Plants of the new *Saturozygis* and the male parent selection differ in flower coloration as plants of the male parent selection have pink-colored flowers.

Plants of the new *Saturozygis* can also be compared to plants of the *Satureja hortensis* cultivar Summer Savory, not patented. In side-by-side comparisons conducted in Bonsall, Calif., plants of the new *Saturozygis* differed from plants of the cultivar Summer Savory in the following characteristics:

1. Plants of the new *Saturozygis* were more vigorous than plants of the cultivar Summer Savory.

2. Plants of the new *Saturozygis* flower for a longer period of time than plants of the cultivar Summer Savory.
3. Plants of the new *Saturozygis* had larger flowers than plants of the cultivar Summer Savory.
4. Plants of the new *Saturozygis* and the cultivar Summer Savory differed in flower coloration as plants of the Summer Savory had whitish purple-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Saturozygis*.

The photograph at the bottom of the sheet comprises a side perspective view of a typical flowering plant of 'Usmint2' grown in a one-gallon container.

The photograph at the top of the sheet comprises a close-up view of a typical flowering stem of 'Usmint2'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were grown under conditions which closely approximate commercial production conditions during the summer in an outdoor nursery in Bonsall, Calif. for about eight weeks in 1-gallon containers. During the production of the plants, day temperatures ranged from 18 to 35° C. and night temperatures ranged from 10 to 21° C.

Botanical classification: *Saturozygis* (*Satureja*× *Hesperozygis*) hybrid cultivar Usmint2.

Parentage:

*Female parent*.—Unnamed selection of *Satureja mexicana*, not patented.

*Male parent*.—Unnamed selection of *Hesperozygis* sp., not patented.

Propagation:

*Type cutting*.—Terminal vegetative cuttings.

*Time to initiate roots*.—About one week.

*Root description*.—Fine, fibrous, and freely branching.

Plant description:

*Form*.—Upright and outwardly spreading plant form; loose, open habit. Freely branching, about eight main stems each with many lateral branches; dense and bushy plant habit; vigorous growth habit and rapid growth rate. Numerous bilabiate tubular flowers arranged in loose axillary verticels.

*Plant height*.—About 35 cm.

*Plant width*.—About 65 cm.

*Lateral branch description*.—Length: About 30 cm. Diameter: About 6 mm. Internode length: About 2.5 cm. Strength: Strong. Aspect: Initially upright, then arching outwardly. Texture: Young, minute pubescence; mature, slightly pubescent. Color, young: 148A. Color, mature: 200B.

*Foliage description*.—Arrangement: Opposite, simple. Length: About 1.4 cm. Width: About 9 mm. Shape: Elliptical. Apex: Acute. Base: Attenuate. Margin: Minutely serrate. Texture, upper and lower surfaces: Smooth, glabrous. Fragrance: Mint-like; spicy. Venation pattern: Pinnate; arcuate. Color: Developing and fully expanded foliage, upper surface: 147A; venation, 147A. Developing and fully expanded foliage, lower surface: 147B; venation, 147C. Petiole length: About 7 mm. Petiole diameter: About 1 mm. Petiole color: 144B.

Flower description:

*Flower arrangement and shape*.—Small single bilabiate tubular flowers arranged in loose axillary verticels. Flowers face mostly outwardly. Freely flowering, about 70 open flowers and flower buds per lateral branch.

*Natural flowering season*.—Flowering continuous from April through October in Southern California.

*Flower longevity on the plant*.—Individual inflorescences last about two weeks on the plant and individual flowers last about five to seven days on the plant. Flowers not persistent.

*Flower buds*.—Length: About 1.4 cm. Diameter: About 2.5 mm. Shape: Elongated oblong. Color: 37D.

*Flowers*.—Diameter: About 8 mm. Depth (height): About 2.2 cm.

*Petals*.—Arrangement: Five, fused into a tube. Length, lobes: About 4 mm. Width, lobes: About 3 mm. Shape: Rounded. Apex: Rounded. Margin: Entire. Texture, upper and lower surfaces: Smooth, velvety. Color: When opening, upper surface: 63C. When opening, lower surface: 63D. Fully opened, upper surface: 63B. Fully opened, lower surface: More gray than 63B.

*Calyx*.—Arrangement: Five sepals fused into a tube. Length: About 9 mm. Width: About 2 mm. Sepal shape: Linear. Sepal apex: Acuminate. Color When opening, upper surface: 143B. When opening, lower surface: 143A. Fully opened, upper and lower surfaces: 146A.

*Pedicels*.—Length: About 3 mm. Diameter: Less than 1 mm. Strength: Moderately strong. Aspect: About 65 to 70° from the stem axis. Color: 148A.

*Reproductive organs*.—Stamens: Quantity per flower: Four. Anther shape: Oval. Anther length: Less than 1 mm. Anther color: 187B. Pollen amount: Scarce. Pollen color: 187B. Pistils: Quantity per flower: One. Pistil length: About 2.5 cm. Stigma shape: Bifurcate. Stigma color: 71B. Style length: About 2.3 cm. Style color: 157A. Ovary color: 145A.

*Seed/fruit*.—Seed and fruit production has not been observed.

Disease/pest resistance: Plants of the new *Saturozygis* have not been noted to be resistant to pathogens and pests common to *Saturozygis*.

Weather tolerance: Plants of the new *Saturozygis* have exhibited good tolerance to rain and wind and have been observed to tolerate temperatures from 0 to 40° C.

It is claimed:

1. A new and distinct cultivar of *Saturozygis* plant named 'Usmint2', as illustrated and described.

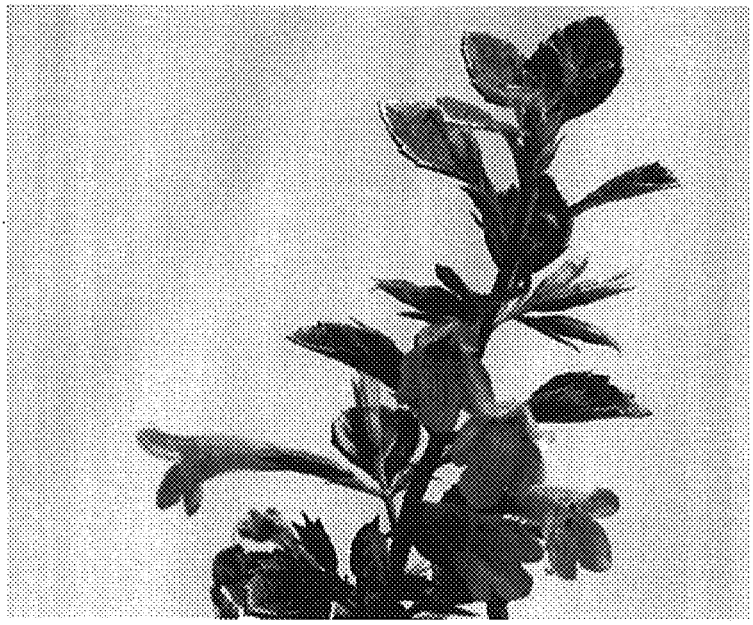
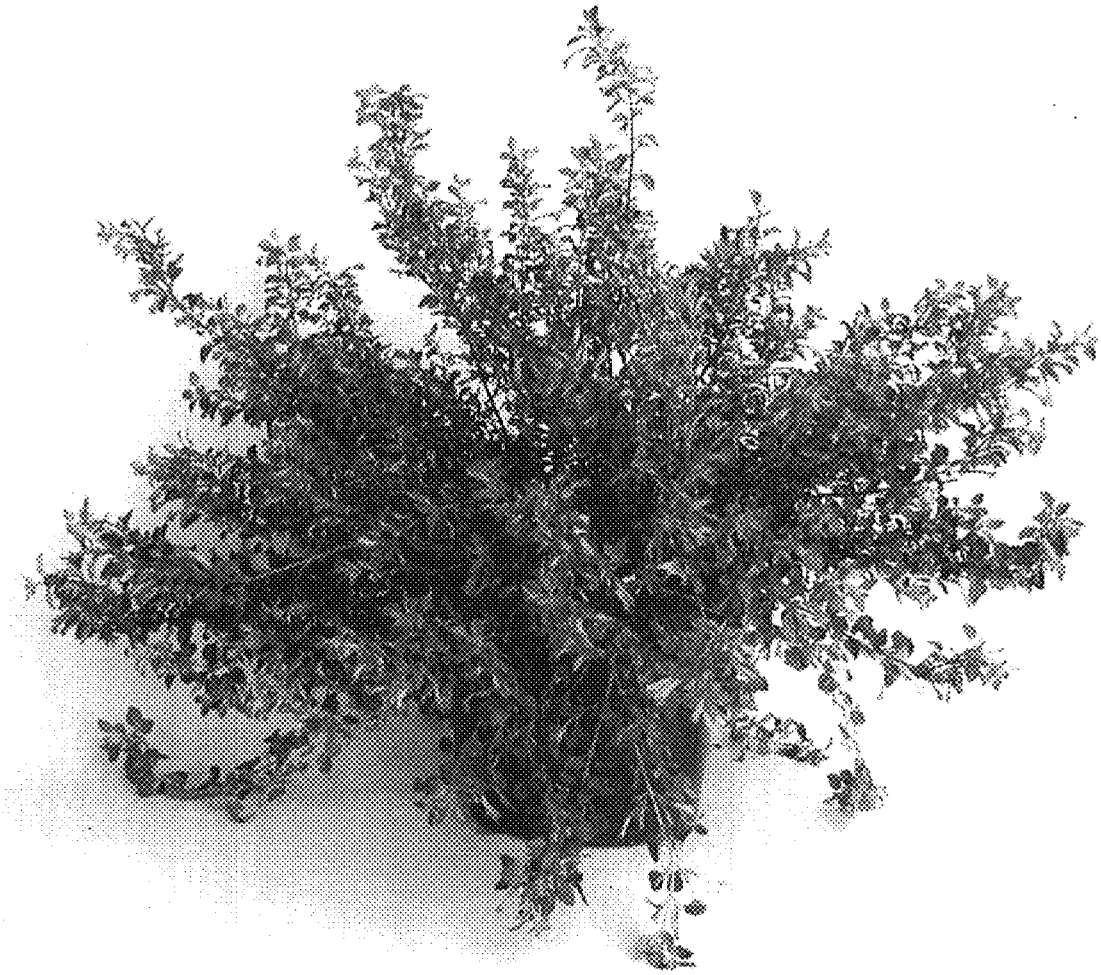

* * * * *